(12) United States Patent
Gorka

(10) Patent No.: US 8,277,756 B2
(45) Date of Patent: Oct. 2, 2012

(54) METHOD OF IDENTIFYING A BLOCKAGE AT THE RECEIVING OPENING OF A PIPETTING NEEDLE

(75) Inventor: Guenther Gorka, Bad Camberg (DE)

(73) Assignee: DiaSys Diagnostic Systems GmbH, Holzheim (DE)

( * ) Notice: Subject to any disclaimer, the term of this patent is extended or adjusted under 35 U.S.C. 154(b) by 100 days.

(21) Appl. No.: 12/312,358

(22) PCT Filed: Oct. 11, 2007

(86) PCT No.: PCT/EP2007/060851
§ 371 (c)(1),
(2), (4) Date: Jun. 12, 2009

(87) PCT Pub. No.: WO2008/055757
PCT Pub. Date: May 15, 2008

(65) Prior Publication Data
US 2010/0028213 A1      Feb. 4, 2010

(30) Foreign Application Priority Data
Nov. 9, 2006   (DE) .......................... 10 2006 052 833

(51) Int. Cl.
*B01L 3/00*      (2006.01)
(52) U.S. Cl. ..................................... 422/501
(58) Field of Classification Search .................. 422/100, 422/501
See application file for complete search history.

(56) References Cited

U.S. PATENT DOCUMENTS 5,365,783 A * 11/1994 Zweifel ...................... 73/304 C (Continued)

FOREIGN PATENT DOCUMENTS
AU     2005211572 A1 *  10/2005
(Continued)

OTHER PUBLICATIONS

PCT/EP2007/060851. English Translation. Download date Nov. 22, 2010, 7 pages.*

*Primary Examiner* — Bobby Ramdhanie
(74) *Attorney, Agent, or Firm* — Gerald K. White

(57) ABSTRACT

A method of identifying a blockage at the receiving opening of a pipetting needle which at or in the proximity of the receiving opening has an electrode (E1) or is itself in the form of an electrode (E1), in an analysis apparatus when taking liquid from a liquid-containing vessel and/or when delivering liquid into a liquid-containing vessel, in which the pipetting needle is displaced in such a way that the receiving opening is immersed in the liquid in the liquid-containing vessel, an amount of liquid is sucked up into the pipetting needle or delivered from the pipetting needle, the pipetting needle is further displaced in such a way that the receiving opening comes out of the liquid in the liquid-containing vessel, during the displacement of the pipetting needle the capacitances ($K_{measurement}$) between the electrode (E1) and a counter-electrode (E2) are detected in dependence on the position of the pipetting needle, the detected capacitances ($K_{measurement}$) are compared to predetermined reference values ($K_{reference}$) for the respective position of the pipetting needle, and information about the presence of a blockage at the receiving opening of the pipetting needle is delivered if the deviation between the detected capacitances ($K_{measurement}$) and the predetermined reference values ($K_{reference}$) at one position or a plurality of positions of the pipetting needle exceeds a predetermined threshold value.

4 Claims, 2 Drawing Sheets

U.S. PATENT DOCUMENTS

| | | |
|---|---|---|
| 5,540,081 A | 7/1996 | Takeda et al. |
| 2005/0092606 A1 | 5/2005 | Reich et al. |

FOREIGN PATENT DOCUMENTS

| | | |
|---|---|---|
| AU | 2005211572 B2 * | 10/2005 |
| DE | 42 03 638 A1 | 8/1993 |
| DE | 199 19 305 A1 | 4/1999 |
| DE | 695 25 570 T2 | 8/2002 |
| EP | 0 819 942 B1 | 4/2001 |
| EP | 0 694 784 B1 | 2/2002 |

* cited by examiner

METHOD OF IDENTIFYING A BLOCKAGE AT THE RECEIVING OPENING OF A PIPETTING NEEDLE

FIELD OF THE INVENTION

The invention concerns a method of identifying a blockage, a coagulum or a clot at the receiving opening of a pipetting needle in an analysis apparatus when taking liquid from a liquid-containing vessel and/or when delivering liquids into a vessel, as well as an analysis apparatus having a device for identifying a blockage, a coagulum or a clot.

RELATED ART AND PROBLEM TO BE SOLVED

In analysis apparatuses which are used in particular for clinical or chemical analysis procedures, liquids are frequently pipetted, the constituents of which can tend to form lumps or coagulate, such as for example blood, serum and the like. Pipetting and dosing of such liquids is effected by way of a pipetting device having at least one pipetting needle which is hollow and has a point, in the proximity of which there is a delivery opening. The pipetting needle is introduced into a sample or measuring vessel and, by means of a connected pump, it can suck in or deliver liquids. Particularly when pipetting liquids which can form coagula or lumps, there is the danger that the pipetting needle becomes blocked. That can have the result inter alia that the amount of liquid which is sucked up or delivered becomes inaccurate and the analysis result is falsified. The coagula, lumps or clots can influence the results for example in spectrometric measurement procedures.

Current analysis apparatuses therefore have a system, by means of which it is possible to identify blockages of the pipetting needle. Upon the delivery or reception of liquid, that system measures an increased pressure or reduced pressure and indicates a blockage when the increased pressure or reduced pressure exceeds a threshold value. That method is suitable for dosing large volumes as in that case large pressure differences occur in the case of a blockage. That system cannot be used for very small volumes as the pressure differences in the case of a blockage are so small, because of the small volumes involved, that the pressure differences can be detected only with very great difficulty or not at all. A further problem in measuring a rise in pressure or a drop in pressure is that fluctuations in the ambient air pressure can influence the result. Moreover, additional pressure sensors are required for that method, whereby the corresponding analysis apparatuses become more expensive.

In comparison the object of the present invention is to provide an inexpensive and reliable method of identifying a blockage, a coagulum or a clot in a pipetting needle when drawing off or delivering liquids, and an analysis apparatus with which that method is carried out. In particular the invention seeks to provide that the method according to the invention and the analysis apparatus are capable of identifying blockages, coagula or clots when dosing small amounts of liquids.

BRIEF SUMMARY OF THE INVENTION

According to the invention that object is attained by a method of identifying a blockage at the receiving opening of a pipetting needle which at or in the proximity of the receiving opening has an electrode (E1) or is itself in the form of an electrode (E1), in an analysis apparatus when taking liquid from a liquid-containing vessel and/or when delivering liquid into a liquid-containing vessel, in which the pipetting needle is displaced in such a way that the receiving opening is immersed in the liquid in the liquid-containing vessel, an amount of liquid is sucked up into the pipetting needle or delivered from the pipetting needle, the pipetting needle is further displaced in such a way that the receiving opening comes out of the liquid in the liquid-containing vessel, during the displacement of the pipetting needle the capacitances ($K_{measurement}$) between the electrode (E1) and a counter-electrode (E2) are detected in dependence on the position of the pipetting needle, the detected capacitances ($K_{measurement}$) are compared to predetermined reference values ($K_{reference}$) for the respective position of the pipetting needle, and information about the presence of a blockage at the receiving opening of the pipetting needle is delivered if the deviation between the detected capacitances ($K_{measurement}$) and the predetermined reference values ($K_{reference}$) at one position or a plurality of positions of the pipetting needle exceeds a predetermined threshold value.

DETAILED DESCRIPTION OF THE INVENTION

When reference is made to a blockage of the pipetting needle in this description or the claims, that term embraces any kind of blockage, inter alia also coagula or clots which can occur by virtue of sucking in particles in the liquid, sucking in coagulated blood constituents or by separations, precipitations or solidification of constituents out of the liquid at the receiving opening of the pipetting needle or within the pipetting needle.

This method is particularly suitable for pipetting and dosing liquids which can coagulate or can form lumps such as for example blood, serum, cell suspensions, protein-bearing solutions, DNA-bearing solutions, gels and slurries.

At or in the proximity of the receiving opening the pipetting needle used to carry out the method has an electrically conductive electrode or is itself in the form of an electrode. The electrode is desirably insulated in relation to the surroundings.

The counter-electrode for measurement of the capacitance can be designed and arranged in various ways. In an embodiment of the invention the counter-electrode is arranged under or beside the liquid-containing vessel. Preferably it is arranged under the vessel. In an alternative embodiment the vessel wall or a part thereof forms the counter-electrode. In that case the vessel wall or a part thereof is of an electrically conductive nature. In a further alternative embodiment the counter-electrode is provided in the dosing needle itself, by for example the electrode being provided at the dosing needle and the counter-electrode being in the form of two coaxially arranged tubes or in the form of a tube and a pin arranged coaxially therein.

Capacitance is the property of a component for storing an electrical energy. The capacitor is the electronic component which has that marked property. The capacitance of a capacitor is determined by its structural sizes. The capacitance is correspondingly greater, the larger the plate or electrode surface, the smaller the plate or electrode spacing and the greater the dielectric constant of the dielectric between the plates or electrodes. The dielectric constant specifies the degree by which the dielectric is better than air.

When the pipetting needle or the electrode goes into aqueous, ion-containing liquid, there is an almost sharp jump-like increase in capacitance. In that region the variation in the capacitance involves the greatest change, in dependence on the position of the pipetting needle. The derivative of the capacitance in accordance with position is at a maximum at that location. In the reverse direction of displacement of the pipetting needle, that is to say when the tip of the pipetting needle is moved out of the liquid, there is a jump-like drop in capacitance.

If a blockage, a coagulum or a clot is disposed at the receiving opening of the pipetting needle, in particular a coagulum which is hanging down from the receiving opening of the pipetting needle, a connection or bridging-over portion can be formed thereby between the liquid and the receiving opening of the pipetting needle, even if the pipetting needle has already been moved out of the liquid. That connection or bridging-over potion between the surface of the liquid and the receiving opening of the pipetting needle is electrically conducting. By way thereof, over a given displacement travel of the pipetting needle, a higher level of capacitance is detected than would be expected without that connection caused by the blockage, and having regard to the level of liquid in the vessel. That expected capacitance is referred to herein as the reference value ($K_{reference}$) and can be easily calculated on the basis of the change in the height of the surface of the liquid in the vessel, such change occurring in dependence on the volume of liquid to be taken from the vessel in the liquid-removal operation, and the dimensions of the vessel. If the deviation between the detected capacitances and the predetermined reference values at a position or a plurality of positions of the pipetting needle exceeds a predetermined threshold value, that is evaluated as indicating the presence of a blockage, a coagulum or a clot and a corresponding item of information is delivered. In a preferred embodiment of the invention the capacitances ($K_{measurement}$) are detected over portions of the displacement travel of the pipetting needle, wherein the portions include at least the travel distance of the receiving opening of the pipetting needle when the receiving opening is moved out of the liquid into the space outside the liquid.

Accordingly measurement of the capacitances includes the portions of the displacement travel of the pipetting needle, in which the greatest change in capacitance occurs and which are particularly relevant for detecting a blockage. By detecting the change in the capacitances during the movement of the pipetting needle into the liquid in the liquid-containing vessel, it is possible to establish whether the liquid-containing vessel actually contains the amount of theoretically contained liquid. By measurement during the movement out of the liquid, it is possible to establish whether, after the removal or delivery operation implemented by the pipetting needle, the liquid theoretically contained in the vessel is in fact present and whether there is a blockage at the receiving opening of the pipetting needle.

In a further preferred embodiment of the invention the capacitances ($K_{measurement}$) are detected over the entire displacement travel of the pipetting needle.

Uninterrupted measurement of the configuration of the change in capacitance makes it possible to precisely monitor liquid delivery and in particular liquid take-up, in which case it is possible to establish in particular when picking up liquid whether the removal opening of the pipetting needle is no longer within the liquid and as a result air is being sucked in. In addition it is also possible in that way to detect air bubbles and larger foam bubbles on the surface of the liquid.

In a further preferred embodiment of the invention the reference values ($K_{reference}$) of the capacitance are determined in dependence on the position of the pipetting needle by a procedure whereby the pipetting needle is displaced in such a way that the receiving opening is immersed in the liquid in the liquid-containing vessel, the pipetting needle is further displaced in such a way that the receiving opening is moved out of the liquid in the liquid-containing vessel without an amount of liquid being sucked up into the pipetting needle, during the displacement of the pipetting needle the capacitances ($K_0$) between the electrode (E1) and a counter-electrode (E2) are detected in dependence on the position of the pipetting needle, and the detected capacitances ($K_0$) are corrected in dependence on the position of the pipetting needle in relation to the change in the height of the surface of the liquid in the vessel, which change occurs in dependence on the liquid volume to be removed in the liquid removal operation and the vessel dimensions, while maintaining the reference values ($K_{reference}$).

If the capacitance between the electrode at the pipetting needle and the counter-electrode is measured when the pipetting needle dips into a liquid or when it comes out of a liquid, a jump in capacitance occurs in both cases. The capacitance variation is subjected in that respect to a hysteresis, that is to say the curves in respect of the variations in capacitance when the pipetting needle dips into the liquid and when it comes out of the liquid are not in coincident relationship but are displaced relative to each other. The jump in capacitance when changing from one medium into another, that is to say from liquid to air and vice-versa, occurs in each case with a certain delay in relation to the actual position of the pipetting needle. The magnitude of the hysteresis effect also depends inter alia on the vessel geometry and the nature of the liquid. The hysteresis involved in the variations in capacitance is to be taken into account when determining the capacitance reference values.

Therefore, for calculating the reference values for the capacitances, at which removal or delivery of liquid is also taken into consideration, it is necessary firstly to determine the capacitances ($K_0$) without liquid removal or delivery. The operation of determining the capacitances ($K_0$) without liquid removal or delivery can be effected individually for each individual sample or can be obtained from comparison data.

In a preferred embodiment of the invention therefore the capacitances ($K_0$) in dependence on the position of the pipetting needle are once detected and stored and the reference values ($K_{reference}$) are calculated having regard to the height of the surface of the liquid contained in the vessel and the change in the height of the surface of the liquid.

The invention further concerns a pipetting apparatus having a device for identifying a blockage at the receiving opening of a pipetting needle when taking liquid from a liquid-containing vessel and/or when delivering liquid into a liquid-containing vessel, wherein the pipetting apparatus includes the following:

a pipetting needle which at or in the proximity of the receiving opening has an electrode (E1) or is itself in the form of an electrode (E1), means for vertical displacement of the pipetting needle, means for applying a reduced pressure in the pipetting needle for sucking up an amount of liquid into the pipetting needle and an increased pressure for delivery of an amount of liquid from the pipetting needle, means for detecting the electrical capacitance between the electrode (E1) and a counter-electrode (E2) in dependence on the displacement position of the pipetting needle, means for comparing the detected capacitances to predetermined reference values for the respective position of the pipetting needle, and means for delivering an item of information about the presence of a blockage at the receiving opening of the pipetting needle if the deviation between the detected capacitances and the predetermined reference values at a position or a plurality of positions of the pipetting needle exceeds a predetermined threshold value.

In addition the invention concerns an analysis apparatus which includes at least one pipetting apparatus of the aforementioned kind.

Such a pipetting apparatus or such an analysis apparatus is suitable in particular for chemical and clinical analysis procedures with the above-mentioned liquids. In that respect it is of particular significance that the samples are not contaminated by relatively large lumps or coagula which can be detected by means of this pipetting apparatus. The pipetting apparatus according to the invention makes it possible to identify in particular blockages of the pipetting needle when very small sample volumes of about 1 to 2 μl are involved. Current methods in which a blockage is detected by pressure measurement are not in a position of identifying blockages with such small sample volumes.

Preferably the pipetting needle is screened in relation to interference capacitances. Capacitances which are caused by surrounding equipment or by components within the analysis apparatus itself can give rise to disturbances in respect of capacitance measurement between the electrode at the pipetting needle and the counter-electrode. It is therefore appropriate for the pipetting needle to be screened in relation to such interference capacitances. A coaxial arrangement for example can be used for screening purposes.

Further advantages, features and embodiments of the invention will be apparent from the description hereinafter and the accompanying Figures.

DETAILED DESCRIPTION OF THE DRAWINGS

Figure 1:
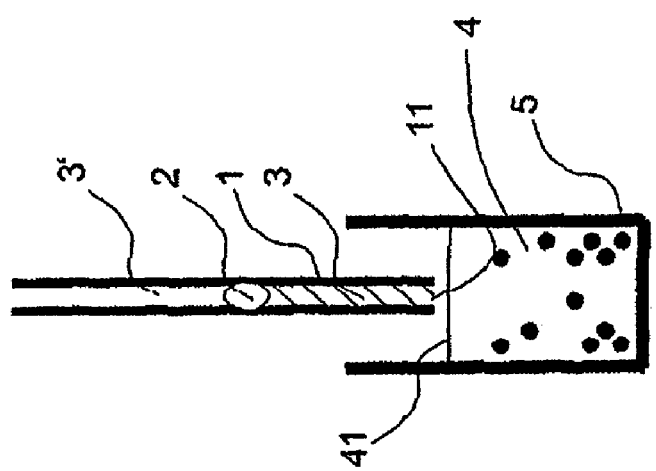
FIG. 1 shows a diagrammatic view of a pipetting needle after moving out of a liquid-containing vessel.

FIG. 1 shows a pipetting needle 1 which includes an air separation bubble 2 for separating the sucked-up liquid 3 from system liquid 3' in the needle. The needle 1 has been moved out of the vessel 5 which contains the liquid 4. There is air between the receiving opening 11 of the pipetting needle 1 and the surface 41 of the liquid.

Figure 2:
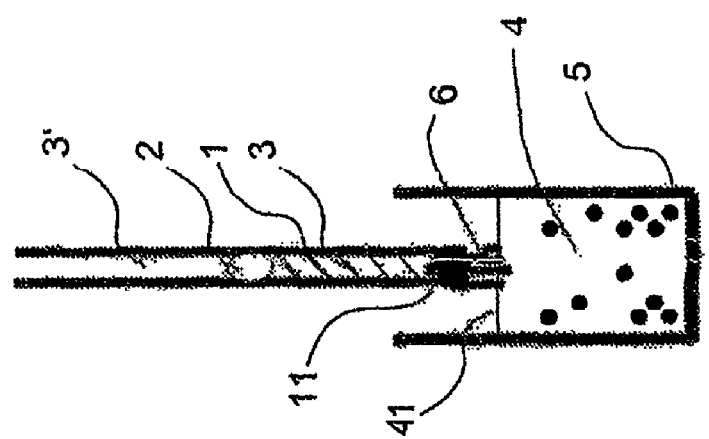
FIG. 2 shows a diagrammatic view of a pipetting needle after moving out of a liquid-containing vessel, wherein there is a clot at the removal opening of the pipetting needle.

FIG. 2 shows a pipetting needle 1 with a sucked-up liquid 3 which has been moved out of a vessel 5 containing liquid 4. In that case, between the receiving opening 11 of the pipetting needle 1 and the surface 41 of the liquid is a clot 6 which makes an electrically conducting connection between the liquids 3 and 4. The capacitance ($K_{measurement}$) between the electrode and the counter-electrode, that is measured with the pipetting needle in that position, thus differs from that which, in the ideal case without the clot, would occur or be expected, that is to say if there were only air ($K_{reference}$) between the pipetting needle 1 and the surface 41 of the liquid, as shown in FIG. 1. The steep jump in capacitance thus occurs only when the receiving opening 11 of the pipetting needle 1 is still further removed from the surface 41 of the liquid and the clot 6 is no longer touching the liquid 4 or the liquid surface 41.

The method according to the invention provides that the clot present in FIG. 2 is identified and a corresponding signal delivered. The pipetting needle can thereupon be fully automatically or semi-automatically flushed through and the sample in question can be discarded or pipetting can be effected once again.

Figure 3:
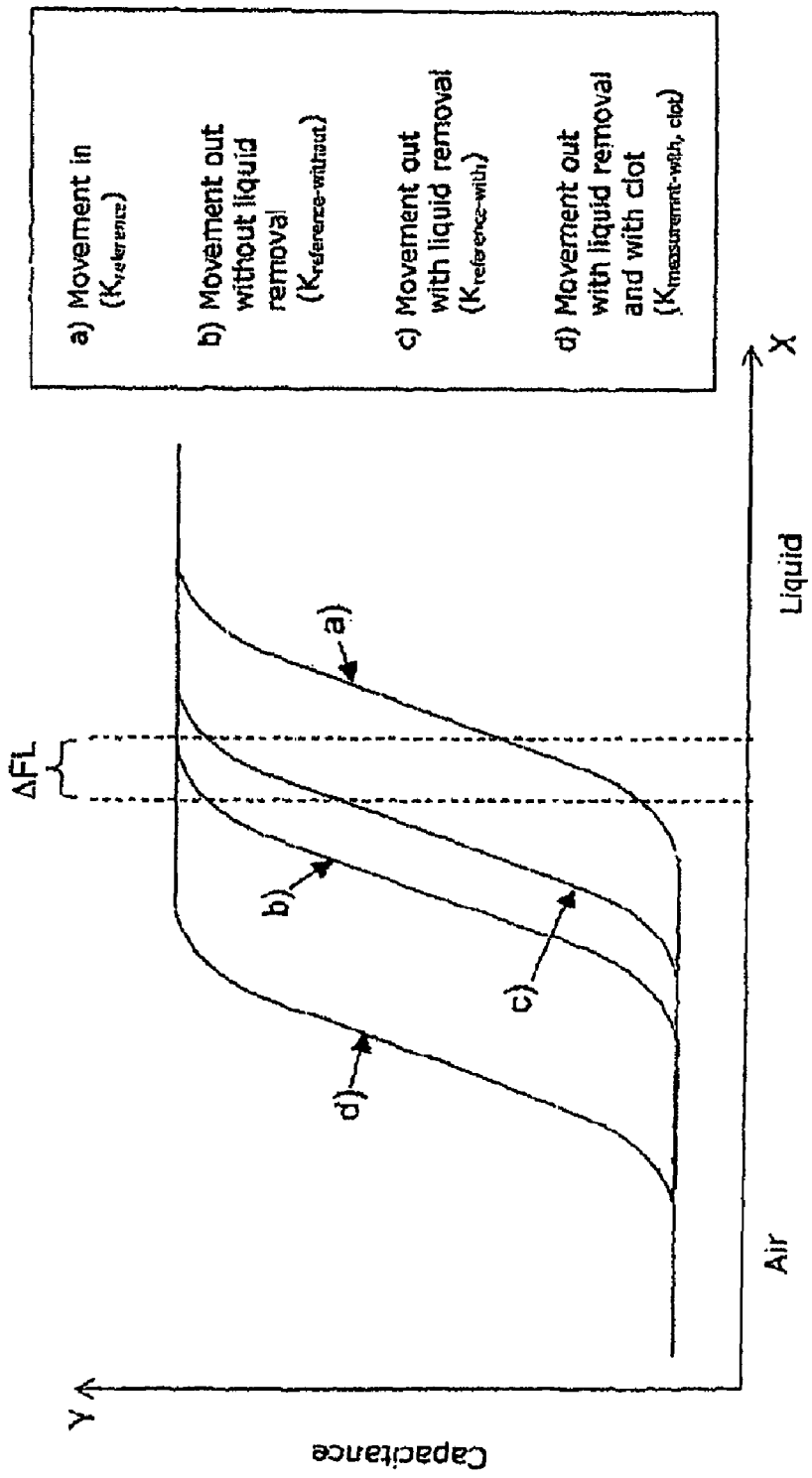
FIG. 3 shows a diagram of the capacitance variations.

FIG. 3 diagrammatically shows the detected capacitances between an electrode at the pipetting needle and a counter-electrode when the pipetting needle moves into a liquid (curve a; $K_{reference}$), when moving out of the liquid without liquid removal (curve b; $K_{reference-without}$), when moving out of the liquid with liquid removal without clot (curve c; $K_{reference-with}$) and when moving out of the liquid with liquid removal and with clot (curve d; $K_{measurement-with,\ clot}$).

The X-axis identifies the vertical position of the receiving opening of the pipetting needle relative to the liquid-containing vessel (without units). The measured capacitance is plotted on the Y-axis (without units).

It is possible to clearly see the steep jumps in capacitance and the hysteresis between the capacitance variations upon movement of the pipetting needle into the liquid and upon movement of the pipetting needle out of the liquid without liquid removal (curves a and b). The measured capacitances of the curves a and b correspond to the reference values of the capacitances in a system involving a given vessel geometry, a given liquid and a given amount of liquid, but still without having regard to a liquid removal operation.

The values measured here are still for an actual liquid removal operation to correct the change in the height of the surface of the liquid upon removal or addition of liquid. The variation in the height of the surface of the liquid is identified by ΔFL in FIG. 3. When liquid is removed the curve b of the capacitances measured without liquid removal is displaced towards the right, that is to say upon movement of the pipetting needle out of the liquid the steep drop in capacitance occurs earlier than without liquid removal. The displacement of the curve in relation to the X-axis corresponds to the variation in the height of the surface of the liquid, which can be easily calculated on the basis of the vessel geometry and the volume removed. The curve c in FIG. 3 shows the variation in capacitances when the pipetting needle is moved out, such variation being corrected for the liquid removal operation.

If a clot or coagulum is detected when removing liquid at the receiving opening of the pipetting needle, then, when the pipetting needle is moved out of the liquid, the steep drop in capacitance only occurs markedly later than without a clot or coagulum (curve c) and the curve in respect of the variation in the actually measured capacitances is displaced towards the left (curve d; $K_{measurement-with,\ clot}$). If the spacing of the detected capacitances ($K_{measurement}$) from the reference values exceeds a predetermined threshold value, that is outputted as information about the presence of a coagulum or clot. It is sufficient for that purpose to compare individual ones or a plurality of capacitance values in the curve regions of the steep changes in capacitance.

The invention claimed is:

1. A method of identifying a blockage at a receiving opening of a pipetting needle in an analysis apparatus when taking liquid from a liquid-containing vessel and/or when delivering liquid into a liquid-containing vessel, said pipetting needle at or close to the receiving opening having an electrode (E1) or being itself an electrode (E1), comprising:

(a) said pipetting needle being displaced such that the receiving opening is immersed in said liquid-containing vessel;
(b) an amount of liquid being sucked up into said pipetting needle or delivered from said pipetting needle;
(c) further displacing said pipetting needle such that the receiving opening comes out of the liquid in the liquid-containing vessel;
(d) detecting during said displacement of the pipetting needle capacitances ($K_{measurement}$) between the electrode (E1) and a counter-electrode (E2) in dependence on the position of said pipetting needle;
(e) comparing the detected capacitances ($K_{measurement}$) to reference values ($K_{reference}$) for the respective position of said pipetting needle; and
(f) delivering information about the presence of a blockage at the receiving opening of the pipetting needle if a deviation between the detected capacitances ($K_{measurement}$) and the reference values ($K_{reference}$) at one position or a plurality of positions of the pipetting needle exceeds a threshold value; whereby said reference values ($K_{reference}$) of the capacitance are determined in dependence on the position of said pipetting needle by a procedure comprising:
(a) the pipetting needle being displaced such that said receiving opening is immersed in said liquid in said liquid-containing vessel;
(b) further displacing said pipetting needle such that said receiving opening is moved out of said liquid in said liquid-containing vessel without an amount of liquid being sucked up into said pipetting needle;
(c) detecting during said displacement of said pipetting needle capacitances (KO) between the electrode (E1) and a counter-electrode (E2) in dependence on the position of the pipetting needle; and
(d) correcting said detected capacitances (KO) in dependence on the position of the pipetting needle in relation to the change in the height of the surface of the liquid in the vessel, which change occurs in dependence on the liquid volume to be removed in the liquid removal operation, and the vessel dimensions, thereby obtaining said reference values ($K_{reference}$).

2. A method according to claim 1, whereby said capacitances ($K_{measurement}$) are detected over the entire displacement travel of the pipetting needle.

3. A method according to claim 1, whereby said capacitances ($K_{measurement}$) are detected over portions of the displacement travel of said pipetting needle, wherein the portions include at least the travel distance of said receiving opening of said pipetting needle when said receiving opening is moved out of said liquid into a space outside said liquid.

4. A method according to claim 1, whereby said capacitances ($K_0$) in dependence on the position of the pipetting needle are once detected and stored and said reference values ($K_{reference}$) are calculated having regard to the height of the surface of the liquid contained in the vessel and the change in the height of the surface of the liquid.

* * * * *